US010258695B2

(12) United States Patent
Raines et al.

(10) Patent No.: US 10,258,695 B2
(45) Date of Patent: Apr. 16, 2019

(54) PROTEIN DERIVATIZATION TO ENDOW CELL PENETRATION

(71) Applicant: Wisconsin Alumni Research Foundation, Madison, WI (US)

(72) Inventors: Ronald T. Raines, Madison, WI (US); Kristen A. Andersen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/845,108

(22) Filed: Sep. 3, 2015

(65) Prior Publication Data

US 2016/0067342 A1    Mar. 10, 2016

Related U.S. Application Data

(60) Provisional application No. 62/046,077, filed on Sep. 4, 2014.

(51) Int. Cl.
*A61K 47/54* (2017.01)
*C07K 1/107* (2006.01)
*C07K 1/13* (2006.01)

(52) U.S. Cl.
CPC ............ *A61K 47/54* (2017.08); *C07K 1/1077* (2013.01); *C07K 1/13* (2013.01)

(58) Field of Classification Search
None
See application file for complete search history.

(56) References Cited

U.S. PATENT DOCUMENTS

| | | | | |
|---|---|---|---|---|
| 8,350,014 | B2 | 1/2013 | Raines et al. | |
| 8,871,916 | B2 | 10/2014 | Raines et al. | |
| 2003/0060399 | A1* | 3/2003 | Brophy | C07K 5/0806 514/7.4 |
| 2009/0324535 | A1* | 12/2009 | Boyd | A61K 31/74 424/78.17 |
| 2016/0297752 | A1 | 10/2016 | Raines et al. | |

OTHER PUBLICATIONS

Anjaneyulu et al. ('Diazofluorene—A new reagent for fluorescent photochemical labelling of membrane hydrophobic core' FEBS Letters v146(1) Sep. 1982 pp. 165-167).*
Bechera et al. ('Cell-penetrating peptides: 20 years later, where do we stand?' FEBS Letters v587 2013 pp. 1693-1702).*
Kaminskas et al. ('Capping methotrexate alpha-carboxyl groups enhances systemic exposure and retains the cytotoxicity of drug conjugated PEGylated polylysine dendrimers' Molecular Pharmaceutics v8 2011 pp. 338-349).*
Correa et al. ('A graph-structural method for prediction of polymer properties' Brazilian Journal of Chemical Engineering v21(4) Oct.-Dec. 2004 pp. 621-628).*
Kamkaew et al. ('Cationic polyfluorenes for intracellular delivery of proteins' Organic and Biomolecular Chemistry v9 2011 pp. 6513-6518) (Year: 2011).*
Bräse et al. (2005) "Organic azides: an exploding diversity of a unique class of compounds," *Angew. Chem. Int. Ed.* 44:5188-5240.
Chibnall et al. (1958) "Studies on the amide and C-terminal residues in proteins. 3. The esterification of proteins," *Biochem. J.* 68:114-118.
De et al. (2009) "Solvent-Promoted and -Controlled Aza-Michael Reaction with Aromatic Amines," *J. Org. Chem.* 74:6260-6265.
Delpierre et al. (1965) "Inactivation of pepsin by diphenyldiazomethane," *Proc. Natl. Acad. Sci. USA.* 54:1161-1167.
Doscher et al. (1961) "Chemical derivatives of alpha-chymotrypsinogen IV. A comparison of the reactions of alpha-chymotrypsinogen and of simple carboxylic acids with diazoacetamidem," *J. Biol. Chem.* 236:1328-1337.
Doyle (1986) "Catalytic methods for metal carbene transformations," *Chem. Rev.* 86:919-939.
Dumitrescu et al. (Jan. 19, 2011) "Nonmetal Catalyzed Insertion Reactions of Diazocarbonyls to Acid Derivatives in Fluorinated Alcohols," *Org. Lett.* 13:692-695.
Froussios et al. (1989) "Novelle Methode De Protection Du Carboxyle Des Acid a-Amine: Esters 9-Fluorenyliques," *Tetrahedron Letts,* 30(26):3413-3414 full reference with English translation.
Furrow et al. (2004) "A general procedure for the esterification of carboxylic acids with diazoalkanes generated in situ by the oxidation of N-tert-butyldimethylsilylhydrazones with (difluoroiodo)benzene," *J. Am. Chem. Soc.* 126:12222-12223.
Grossberg et al. (1960) "Nature of the Combining Site of Antibody against a Hapten Bearing a Positive Charge," *J. Am. Chem. Soc.* 82:5478-5482.
Jewett et al. (2010) "Rapid Cu-Free Click Chemistry with Readily Synthesized Biarylazacyclooctynones," *J. Am. Chem. Soc.* 132:3688-3690.
Larson et al. (1981) "Stabilization of charged substrates by first- and second-row heteroatoms," *J. Am. Chem. Soc.* 103:410-416.

(Continued)

*Primary Examiner* — Karlheinz R. Skowronek
*Assistant Examiner* — Ronald T Niebauer
(74) *Attorney, Agent, or Firm* — Leydig, Voit & Mayer, Ltd.

(57) ABSTRACT

Methods and reagents for enhancing cellular uptake of a cargo molecule by covalently bonding optionally-substituted fluorenyl groups to the cargo molecules, where cellular uptake includes at least partial uptake into the cytosol. Useful fluorenylation reagents include those of formula:

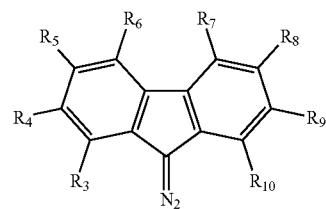

and salts thereof where variables are as defined. Cargo molecules include peptides and proteins. Also provided are fluorenylated cargo molecules, including fluorenylated peptides and proteins.

13 Claims, 3 Drawing Sheets

(56) References Cited

OTHER PUBLICATIONS

Matthews et al. (1975) "Equilibrium acidities of carbon acids. VI. Establishment of an absolute scale of acidities in dimethyl sulfoxide solution," *J. Am. Chem. Soc.* 97:7006-7014.

McGarrity et al. (1980) "Hydrolysis of diazomethane-kinetics and mechanism," *J. Am. Chem. Soc.* 102:7303-7308.

McGrath et al. (Aug. 2, 2012) "Diazo compounds as highly tunable reactants in 1,3-dipolar cycloaddition reactions with cycloalkynes," Chem. Sci. 3:3237-3240.

Myers et al. (2009) "A phosphine-mediated conversion of azides into diazo compounds," *Angew. Chem. Int. Ed.* 48:2359-2363.

Riehm et al. (1965) "Structural Studies of Ribonuclease. XVII. A Reactive Carboxyl Group in Ribonuclease," *Biochemistry.* 4:772-782.

Szele et al. (1983) "Reactions of Alkenediazonium Salts. Part 1. 2,2-Diethoxyethene-diazonium hexachloroantimonate: A diazonium, a carbenium or an oxonium salt?" *Helv. Chim. Acta.* 66:1691-1703.

Taft et al. (1988) "Structural and solvent effects evaluated from acidities measured in dimethyl sulfoxide and in the gas phase," *Acc. Chem. Res.* 21:463-469.

Tian et al. (Mar. 12, 2012) "Selective esterase-ester pair for targeting small molecules with cellular specificity," *Proc. Natl. Acad. Sci. USA.* 109:4756-4761.

Ye et al. (1994) "Organic Synthesis with α-Diazo Carbonyl Compounds," *Chem. Rev.* 94:1091-1160.

Andersen K. et al. (Feb. 6, 2015) "Diazo Groups Endure Metabolism and Enable Chemoselectivity in Cellulo," J. Am. Chem. Soc. 137:2412-2415.

Josa-Cullere et al. (Oct. 14, 2014) "Diazo group as a new chemical reporter for bioorthogonal labelling of biomolecules," RSC Adv. 4:52241-52244 (Royal Society of Chemistry).

Mix K.A. and Raines, R.T. (May 4, 2015) "Optimized Diazo Scaffold for Protein Esterification," Organic Letts. 17:2358-2361.

Fuchs, S.M. and Raines, R.T. (2007)"Arginine Grafting to Endow Cell Permeability" ACS Cell Biology vol. 2(3):167-170.

T. E. Ballard, Jr., "Small molecule control of biological function," Dissertation submitted to North Carolina State University, 2008 (in 2 parts).

Chou et al. (Sep. 23, 2013) "Conversion of Azides into Diazo Compounds in Water," J. Am. Chem. Soc. 135:14936-14939.

Friedrich E.C. and Taggart D. B. (1978) "Comparisons of the Inden-1-yl, Fluoren-9-yl, and Cycloprop[2,3]inden-1-yl Cations," J. Org. Chem. 43:805-808.

McGrath, N.A. et al. (Jan. 2015) "Diazo compounds for the bioreversible esterification of proteins," Chem. Sci. 6, 752-755.

Mix, K.A. et al. (Oct. 2016) "Diazo Compounds: Versatile Tools for Chemical Biology," ACS Chemical Biology 11(12):3233-3244.

\* cited by examiner

PROTEIN DERIVATIZATION TO ENDOW CELL PENETRATION

CROSS-REFERENCE TO RELATED APPLICATIONS

This application claims the benefit of U.S. provisional application 62/046,077, filed Sep. 4, 2014 which is incorporated by reference in its entirety herein.

STATEMENT REGARDING U.S. GOVERNMENT FUNDING

This invention was made with government support under GM044783 awarded by the National Institutes of Health. The government has certain rights in the invention.

BACKGROUND OF THE INVENTION

The utility of many biologic drugs is limited by inefficient cellular delivery [1]. Previous efforts to overcome this limitation have focused largely on the use of cationic domains, including peptidic cationic species (e.g., HIV-TAT, penetratin, and nonaarginine and more generally cell penetrating peptides (CPP), which are also called protein transduction domains (PTDs)) or non-peptidic cationic species (e.g., PAMAM dendrimers and polyethylenimine), to enhance the attraction between a chemotherapeutic agent and the anionic cell surface [2]. Natural ligands (e.g., folic acid, substance P, and the RGD tripeptide) have also been used to facilitate cellular delivery by targeting agents to specific cell-surface receptors [3]. Such methods have been applied, for example, to delivery of peptides, proteins, nucleic acids and analogs thereof, reporters and labels, various pharmaceuticals and drugs and various small molecules as well as particles. Although some of these methods have had some success, there remains a need in the art for additional delivery strategies. There is a particular need for methods and reagents which facilitate delivery of biologic drugs, particularly peptides and proteins, to the cytosol of cells.

Only a small percentage (<10%) of the extracellular biologics, such as peptides and proteins, that enter endosomes ever get to the cytosol. There is little value in entering endosomes without entering the cytosol.

There are no known methods for modifying a peptide or protein (which does not naturally enter a cell, such as a CPP) to enable its efficient uptake into the cytosol of cells in a bioreversible manner. Being able to do so has many implications for biological research as well as the clinic. For example, dysfunctional proteins could be replaced with functional ones, and misbehaving proteins could be antagonized with specific antibodies. The targeting of antibodies to the cytoplasm is of particular interest [4].

SUMMARY OF THE INVENTION

The present invention relates to methods for enhancing cellular uptake of a cargo molecule by covalently bonding optionally-substituted fluorenyl groups to the cargo molecules, particularly by formation of one or more optionally-substituted fluorenyl ester groups on the cargo molecule. The fluorenylated cargo molecule is then contacted with a cell or tissue containing a cell for uptake. In a specific embodiment, cellular uptake includes at least partial uptake into the cytosol. Cellular uptake may be in vivo or in vitro. The method of the invention is generally useful for the delivery of any desired molecule, e.g., a biologic or other therapeutic, into a cell and specifically includes nucleic acids and analogs thereof; nucleotides and analogs thereof; peptides and proteins; drugs (e.g., anticancer drugs, alkylating agents, antimetabolite, cytotoxic agents; antibiotics, and the like); or reporter molecules or labels (e.g., fluorescent labels, isotopic labels, imaging agents, quantum dots, and the like). In a specific embodiment, the cargo comprises a quantum dot carrying appropriate functionality. The cargo molecule can include combinations of the chemical species listed above, wherein the species are bonded to each other, particularly where the species are covalently bonded to each other. For example, a cargo molecule may combine a peptide, such as a CPP or a nuclear localizing signal, with a nucleic acid, or combine a fluorescent, isotopic or other label with a nucleic acid and or peptide. In a specific embodiment, the cargo is or comprises a molecule which affects, regulates or modulates gene expression in the cell, including a molecule which inhibits or decreases gene expression or a molecule which initiates or enhances gene expression. In a specific embodiment, the cargo is a peptide or a protein, for example, an enzyme.

In a specific embodiment, the optionally substituted fluorenyl group is a 9H-fluoren-9-yl group, bonded through carbon 9 (using standard ring numbering) of the fluorene ring. In specific embodiments, the cargo molecule is fluorenylated to contain 4 or more, 5 or more, 10 or more or 20 or more optionally substituted fluorenyl groups, particularly, 9-H-fluoren-9-yl groups. In more specific embodiments, the peptide or protein is fluorenylated to contain 2-10 or more optionally-substituted fluorenyl groups, particularly 9-H-fluoren-9-yl groups. In specific embodiments, the cargo molecule is fluorenylated to contain a single optionally-substituted fluorenyl group (e.g., 9H-fluoren-9-yl). In additional embodiments, the peptide or protein is fluorenylated to contain 1-3 optionally-substituted fluorenyl groups, particularly 9-H-fluoren-9-yl groups. In additional embodiments, the peptide or protein is fluorenylated to contain 1-5 optionally-substituted fluorenyl groups, particularly 9-H-fluoren-9-yl groups. Fluorenylated peptides and proteins include mixtures of fluorenylated peptides or proteins having different numbers of fluorenyl groups or different sites of fluorenylation. A given fluorenylated peptide can be a mixture in which the peptide contains different numbers and sites of fluorenylation. A given fluorenylated protein can be a mixture in which the protein contains different numbers and sites of fluorenylation.

More specifically, the invention provides a method for improved delivery of a cargo molecule to a eukaryotic cell, particularly a mammalian cell, which comprises the step of contacting the cell or tissue containing the cell with a fluorenylated cargo molecule. In a specific embodiment, the step of contacting the cell or tissue is conducted in vitro. In a specific embodiment, the step of contacting the cell or tissue is conducted in vivo. In a specific embodiment, the fluorenylated cargo molecule comprises a fluorenylated oligopeptide moiety of this invention. In specific embodiments, the cargo molecule carries two or more fluorenyl groups. In specific embodiments, the cargo molecule is a peptide or protein which is fluorenylated by reaction at one or more carboxylate groups in the peptide or protein. In a specific embodiment, the cargo protein is an enzyme. In a specific embodiment, the cargo protein is a fluorescent protein. In a specific embodiment, the cargo peptide or protein is not itself glycosylated (i.e., is not a glycoprotein). In a specific embodiment, the fluorenylated cargo peptide or protein retains at least 10% of a selected biological activity of the peptide or protein prior to fluorenylation. In a specific embodiment, the fluorenylated cargo enzyme retains at least 10% of the activity of the enzyme prior to fluorenylation. In another specific embodiment, the cargo peptide or protein is an antibody or functional fragment thereof and more specifically is a monoclonal antibody or functional fragment thereof.

In specific embodiments, the present invention provides a method of increasing cellular uptake of a peptide or protein by covalently attaching one or more optionally-substituted fluorenyl groups to the peptide or protein. More specifically, the fluorenyl group is covalently attached to the peptide or protein by reaction of a 9-diazofluorene of formula I with one or more carboxylate groups of the peptide or protein. More specifically, cellular uptake is at least in part uptake into the cyctosol of a cell. In specific embodiments, the cell is a mammalian cell. In specific embodiments, the cell is in vitro.

Diazofluorenes useful in this invention include those of formula I:

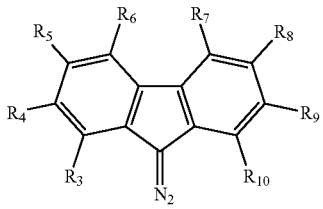

and salts thereof, wherein:

$R_3$-$R_{10}$ are selected from hydrogen, alkyl, alkoxy, alkenyl, alkenoxy, alkynyl, alkynoxy, aryl, aryl oxy, alkylaryl, alkylaryloxy, aryl alkyl, arylalkyloxy, heteroaryl, heteroaryloxy, carbocyclic, carbocyclyloxy, heterocyclic or heterocyclyloxy groups each of which is optionally substituted; or $R_3$-$R_{10}$ are selected from non-hydrogen substituents, including halogens (e.g., Br—, I—, Cl—, F—), hydroxyl (—OH), nitro groups (—NO$_2$), cyano (—CN), isocyano (—NC), hiocyano (—SCN), isothiocyano (—NCS), sulfuryl (—SO$_2$), —N(R')$_2$, —COR', —COOR', —CON(R)$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups; or two of $R_3$-$R_{10}$ are linked together to form an optionally substituted carbocyclic, aryl, heterocyclic or heteroaryl ring wherein one or two carbons of the ring can be replaced with —CO— and the carbocyclic or heterocyclic rings can be saturated or unsaturated.

In a specific embodiment, all of $R_3$-$R_{10}$ are hydrogens. In a specific embodiment, all except one of $R_3$-$R_{10}$ are hydrogens. In a specific embodiment, one or more of $R_3$-$R_{10}$ are selected from hydrogen, alkyl groups having 1-3 carbon atoms, halogens, —N(R')$_2$, —COR', —COOR', —CON(R')$_2$, —NR'—CO—R', —NR—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups. In a specific embodiment, one or more of $R_3$-$R_{10}$ is a —NR'—CO—R' group.

In specific embodiments, $R_3$-$R_{10}$ are selected from hydrogen, halogen, or alkyl groups having 1-3 carbon atoms. In specific embodiments, $R_3$-$R_{10}$ are selected from hydrogen, chlorine, bromine, iodine, fluorine or alkyl groups having 1-3 carbon atoms. In specific embodiments, $R_3$-$R_{10}$ are selected from hydrogen, halogen, or methyl groups. In specific embodiments, one or two of $R_3$-$R_{10}$ are selected from non-hydrogen substituents and the remaining R groups are hydrogens. In specific embodiments, one or two of $R_3$-$R_{10}$ are selected from halogen, or alkyl groups having 1-3 carbon atoms and the remaining R groups are hydrogen. In specific embodiments, one or two of $R_3$-$R_{10}$ are selected from halogen, or methyl groups and the remaining R groups are hydrogen.

In a specific embodiment, one or both of $R_4$ and $R_9$ are —NR'—CO—R' groups. In specific embodiments, the —NR'—CO—R' groups are —NH—CO—R' groups where R' is an alkyl group or a haloalkyl group, and more specifically where R' is a methyl group or a trifluoroethyl group. In specific embodiments, none of $R_3$-$R_{10}$ are —NR'—CO—R' groups. In specific embodiments, none of $R_3$-$R_{10}$ are amine or amide groups. In specific embodiments, none of $R_3$-$R_{10}$ are isocyanate groups.

In specific embodiments, the fluorenyl group can itself exhibit fluorescence.

In specific embodiments, fluorenylated oligopeptides, peptides and proteins of this invention have formula II:

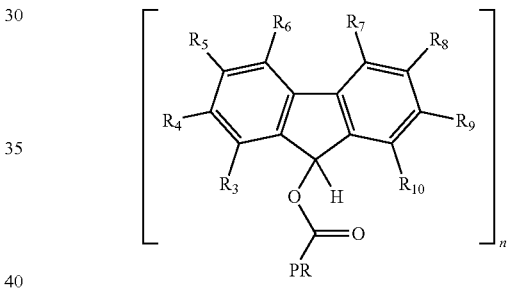

and salts thereof, where $R_3$-$R_{10}$ are as defined for formula I, PR is the oligopeptide, peptide or protein and n is the number of optionally substituted fluorenyl groups covalently bonded to the protein or peptide. In specific embodiments, n is 1. In specific embodiments, n is 2. In specific embodiments, n is 3. In specific embodiments, n is 1-5. In specific embodiments, n is 1-10. An optionally substituted fluorenyl group is bonded to the protein or peptide via an ester linkage as illustrated in formula II. In an embodiment, an optionally substituted fluorenyl group is bonded through an ester linkage to an amino acid side chain carboxylate group (—COOH/—COO$^-$) of the protein or peptide. In an embodiment, an optionally substituted fluorenyl group is bonded through an ester linkage to a carboxy terminus (—COOH/—COO$^-$) of the protein or peptide. In specific embodiments, PR is an oligopeptide. In specific embodiments, PR is an oligopeptide and n is 1 or 2.

In specific embodiments, the cargo molecule is fluorenylated to contain 2 or more, 4 or more, 5 or more, 10 or more or 20 or more fluorenyl groups. In more specific embodiments, the peptide or protein contains 2-10 fluorenyl groups.

In specific embodiments, $R_3$-$R_{10}$ are selected from hydrogen, halogen, or alkyl having 1-3 carbon atoms. In specific embodiments, $R_3$-$R_{10}$ are selected from hydrogen, fluorine, or methyl groups. In specific embodiments, one or two of $R_3$-$R_{10}$ are selected from halogen or alkyl groups having 1-3 carbon atoms and the remaining R groups are hydrogens. In specific embodiments, either of $R_4$ or $R_9$ are non-hydrogen substituents as defined above and the remaining R groups are hydrogen. In specific embodiments, either or both of $R_4$ and $R_9$ are halogens or alkyl groups having 1-3 carbon atoms and the remaining R groups are hydrogens. In specific embodiments, $R_4$ and/or $R_9$ are chlorine or bromine and the remaining R groups are hydrogen. In specific embodiments, $R_4$ and/or $R_9$ are methyl groups and the remaining R groups are hydrogen. In specific embodiments, one of $R_3$-$R_{10}$ is selected from halogen, alkyl having 1-3 carbon atoms and the remaining R groups are hydrogen.

In additional embodiments, the invention provides side-chain fluorenylated amino acids of formula IIA wherein the fluorenyl group is optionally substituted:

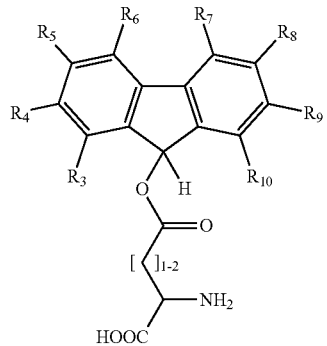

IIA and salts thereof, where $R_3$-$R_{10}$ are as defined above and in a specific embodiment are all hydrogen. In specific embodiments, the compounds of formula IIA are 9H-fluoren-9-yl esters of L-aspartic acid or L-glutamic acid. Optionally substituted fluorenylated amino acids of this invention can be employed in preparation of fluorenylated peptides and proteins. In an additional embodiment, the invention provides a method for preparation of fluorenylated peptides, and/or fluorenylated oligopeptides by solid phase peptide synthesis employing fluorenylated and protected amino acids.

The invention further provides kits for enhanced cellular uptake of a peptide or protein which comprises one or more of the optionally substituted diazofluorenes of formula I, or one or more of the fluorenylated oligopeptide reagents or fluorenylated amino acids of the invention which are individually packaged therein in selected amounts for use in fluorenylating one or more peptides or proteins for enhanced uptake. The invention also provides kits for fluorenylation of a peptide or protein which comprise one or more of the optionally substituted diazofluorene compounds of formula I or one or more of the fluorenylated oligopeptide reagents or one or more fluorenylated amino acids of the invention which are individually packaged therein in selected amounts. Reagent kits may further comprise one or more solvents or reagents for carrying out binding, ligation, crosslinking or reaction of an optionally substituted diazofluorene or fluorenylated oligopeptide or fluorenylated amino acid with a selected peptide or protein. Kits for enhanced cellular uptake may further comprise one or more selected peptides or proteins to be delivered to cells, optional reagents for labeling the peptide or protein, or reagents, media or solvents for contacting cells with the fluorenylated peptide or protein.

DETAILED DESCRIPTION OF THE INVENTION

Figure 1A:
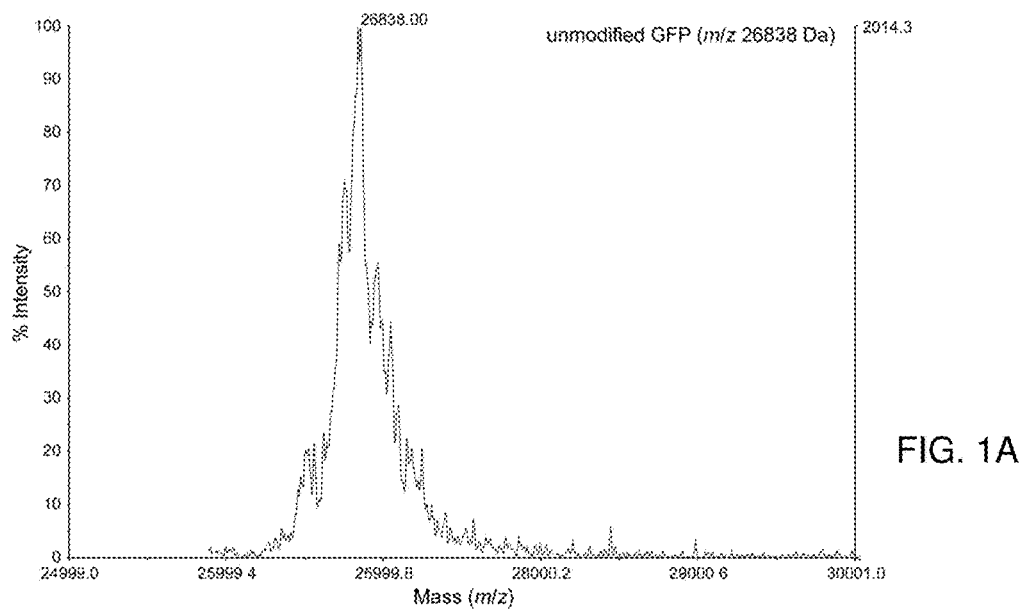
FIGS. 1A and 1B illustrate mass spectra (MALTDI-TOF) of GFP (FIG. 1A) and fluorenyl labelled GFP (FIG. 1B) showing that labeling with diazofluorene for 24 h at room temperature yielded 1-3 fluorenyl groups per GFP.

The invention is based at least in part on the demonstration that derivatization of cargo molecules, specifically peptides and proteins with fluorenyl groups mediate the delivery of the cargo molecules into mammalian cells and at least in part into the cytosol of those cells. More specifically, bonding of one or more optionally-substituted fluorenyl groups to such cargo molecules, particularly peptides or proteins, generally enhances uptake of the fluorenylated cargo molecule into mammalian cells. Additionally, in specific embodiments, the fluorenylated cargo molecule retains biological activity of the corresponding non-fluorenylated cargo molecule.

The terms "fluorenylation" and "fluorenylated" are used generically herein to refer to derivatization of a cargo molecule with one or more optionally-substituted fluorenyl groups. Fluorenyl groups are monovalent groups formally derived from an optionally-substituted fluorene by cleavage of a bond from a ring carbon to a hydrogen or a non-hydrogen substituent. Formula A illustrates an optionally-substituted fluorene:

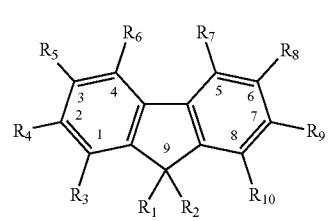

A where standard numbering of ring carbons is shown, and $R_1$-$R_{10}$ represent hydrogen or non-hydrogen substituents, particularly as defined for formula I herein. $R_1$ and $R_2$ are most generally hydrogen or any of the substitutents listed for the $R_3$-$R_{10}$ groups in formula I. $R_1$ and $R_2$ together in formula I are $=N_2$ (a diazo moiety). Fluorenyl groups can be formed formally by removal of any of $R_1$-$R_{10}$. In a specific embodiment, a fluoren-9-yl group (B) is formed by removal of $R_1$ or $R_2$, and when the remaining $R_1$ or $R_2$ is hydrogen the fluoren-9-yl group is more specifically designated optionally-substituted 9H-fluoren-9-yl and when all of $R_2$-$R_{10}$ are hydrogen, the group is designated 9H-fluoren-9-yl (B1).

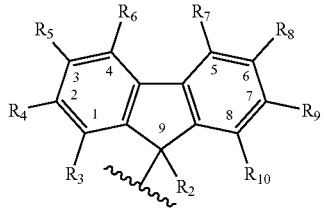

B

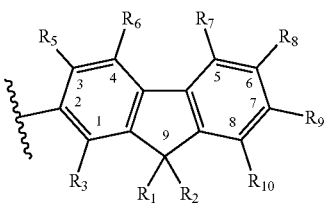

B1

Fluorenyl groups formed at other ring carbons are analogously named. An optionally-substituted fluoren-2-yl group is illustrated as formula C:

C

When all of $R_1$-$R_{10}$ (if present) in the fluorenyl group are hydrogen, the fluorenyl groups include: 9H-fluoren-9-yl, fluoren-1-yl, fluoren-2-yl, fluoren-3-yl, and fluoren-4yl. When substitution is present on the ring, the naming of the groups will depend upon the site(s) of substitution as is known and understood in the art.

In specific embodiments, fluorenylation is accomplished by reaction of a diazofluorene of formula I with one or more carboxylate groups of the cargo molecule. In a specific embodiment, peptides and proteins are fluorenylated by reaction of one or more compounds of formula I with one or more amino acid side chain carboxylates of the peptide or protein (e.g., aspartic acid or glutamic acid groups).

As described in U.S. patent application Ser. No. 14/212,381, filed Mar. 14, 2014 which is incorporated by reference herein in it entirety, it has been found that selectivity and reactivity of an organodiazo compound of formula:

$$\underset{R_2}{\overset{R_1}{>}} = N_2$$

for esterification of carboxylic acids in aqueous solution are correlated with the pKa of the C—H of the corresponding organic compound $R_1(R_2)CH_2$ in DMSO. [8] Thus, diazo-compounds most useful for esterification of carboxylic acid can be selected by measurement or estimation of the pKa of such corresponding non-diazo compounds in DMSO. It is noted that the pKa's of a large number of organic compounds as measured in DMSO have been reported.[8] The pKa's of additional organic compounds can be measured in DMSO employing the methods described in the art.[8] Data already acquired by measurement of pKa's in DMSO that is publicly available in the literature [See, for example, www-.chem.wisc.edu/areas/reich/pkatable/] can in addition be used to estimate the pKa's of structurally analogous compounds for which data is not yet available.

Organodiazo compounds wherein this formal precursor $R_1(R_2)CH_2$ has a pKa less than 18 as measured in DMSO were found to be unreactive under the conditions of esterification as described in the '381 application. Organodiazo compounds wherein this formal precursor has a pKa greater than 29 as measured in DMSO are generally too reactive under the conditions of esterification in the '381 application, are not chemoselective for reaction with carboxylic acid groups and will react with functional groups other than carboxylic acids, e.g., hydroxyl groups, such as are found in serine, threonine and tyrosine side groups. Additionally, the organodiazo compounds of the '381 application were found to be unreactive, under the conditions employed in methods herein, with other common functional groups present in biological systems, e.g., amines, alcohols and thiols.

Thus, diazo compounds of formula I which are preferred for use in fluorenylation reaction to form esters with peptides or protein or other cargo molecules are those wherein the formal precursor of the diazo compound as illustrated above (i.e., $R_1(R_2)CH_2$) exhibits or is calculated to have a pKa in DMSO between 18 and 29 or more specifically between 20 and 24.

Diazofluorene compounds of formula I are prepared, as illustrated in the Examples, from readily available starting materials and reagents. Such starting materials and reagents are commercially available or can be prepared from readily available materials by methods that are well-known in the art. More detail of the synthesis of diazofluorene compounds is found in U.S. Pat. No. 8,350,014 which is incorporated by reference herein in its entirety for descriptions of synthesis and reactivity of diazo compounds.

In specific embodiments, the optionally substituted fluorenyl groups used for fluorenylation of cargo molecules do not themselves exhibit fluorescence. In specific embodiments, substituted fluorenyl groups used for fluorenylation of cargo molecule exhibit fluorescence.

In other specific embodiments, a fluorenylated amino acid or a fluorenylated oligopeptide can be modified, for example, to contain a ligand which selectively binds to the cargo peptide or protein, such as biotin or a derivative thereof such as biocytin.

In another alternative method, the fluorenylated oligopeptide can be coupled to a cargo molecule employing a crosslinking reagent which may contain two or more reactive groups for crosslinking. Homobifunctional and heterobifunctional crosslinking reagents are particularly useful. For example, the fluorenylated oligopeptide can be coupled to the cargo molecule employing a homobifunctional crosslinking reagent or a heterobifunctional crosslinking reagent.

More generally, heterofunctional crosslinking reagents may include a plurality of reactive groups which are the same and one or more different reactive groups. Use of such heterofunctional crosslinking reagents will allow, for example, linking of two or more optionally substituted fluorenyl groups to a single cargo molecule.

An overview of bioconjugation methods that can be employed for fluorenylation of peptides and proteins is found in Hermanson, G. T. Bioconjugation Techniques (2nd Ed.) 2008 Academic Press/Elsevier London, UK. This reference also contains detailed descriptions of homobifunctional and heterobifunctional crossing linking reagents which can optionally be employed to covalently attach an optionally-substituted fluorenyl group to an amino acid, peptide or protein.

In another embodiment, fluorenylation of an oligopeptide for attachment to a cargo molecule or fluorenylation of a cargo peptide or protein can be accomplished by introduction of one or more fluorenylated amino acids (e.g., fluorenylated L-aspartic acid or fluorenylated L-glutamic acid) into the peptide or protein. Fluorenylated amino acids can be introduced onto the peptide or protein directly by solid phase peptide synthesis, wherein one or more of the amino acid derivatives employed for peptide synthesis are fluorenylated. Alternatively, a fluorenylated oligopeptide can be generated by solid phase peptide synthesis employing one or fluorenylated amino acids as starting materials for peptide synthesis. The fluorenylated oligopeptide can be a fluorenylated cargo molecule (where the cargo molecule is the oligopeptide) or the fluorenylated oligopeptide can thereafter be bound to, ligated to or crosslinked to the cargo molecule which is to be fluorenylated.

Fluorenylated oligopeptides useful for fluorenylating cargo molecule can include those having 2-30 amino acids and more specifically those having 5 to 20 amino acids. Fluorenylated oligopeptides include those where 60% or less, 50% or less, 40% or less, or 25% or less of the amino acids of the oligopeptide carry an optionally substituted fluorenyl group. Fluorenylated oligopeptides include those carrying 1, 2, 3, 4, 5, 6, 7, 8, 9, or 10 optionally substituted fluorenyl groups. Fluorenylated oligopeptides include those comprising one or more glutamic acids and/or aspartic acids which are fluorenylated, specifically which are fluorenyl esters.

The term "enhancement of cellular uptake" refers to enhancement of uptake of a fluorenylated cargo molecule compared to uptake of the analogous non-fluorenylated cargo molecule. Enhancement of cellular uptake can be measured by any art-known method and useful methods are exemplified in the examples. In specific embodiments, enhancement of cellular uptake of 2-fold or higher relative to the non-fluorenylated cargo molecule is obtained. Enhancement of cellular uptake may be assessed in terms of % internalization compared to non-fluorenylated cargo molecule. In specific embodiments, enhancement of % internalization of 50% or more compared to controls is obtained. As noted above cellular uptake can at least include uptake into the cytosol. Enhancement of uptake into the cytosol can be measured by any art-known method and useful methods are exemplified in the examples. In specific embodiments, enhancement of uptake cytosol uptake of 2-fold or higher relative to the non-fluorenylated cargo molecule is obtained. Enhancement of cytosol uptake may be assessed in terms of % internalization into the cytosol compared to non-fluorenylated cargo molecule. In specific embodiments, enhancement of % internalization into the cytosol of 50% or more compared to controls is obtained.

The invention provides a method for improved delivery of a cargo molecule, for example, a nucleic acid, peptide or protein, to a cell which comprises the step of contacting the cell or tissue containing the cell with a cargo molecule, for example a nucleic acid, peptide or protein, derivatized with one or more optionally substituted fluorenyl groups, particularly optionally substituted 9H-fluoren-9-yl groups and more particularly 9H-fluoren-9-yl groups. Any methods known in the art for contacting a cell or tissue containing the cell can be employed which will bring the fluorenylated cargo molecule into the vicinity of the cell or tissue. Contacting may occur in vitro by addition of a solution containing the fluorenylated cargo molecule to a solution or medium containing or supporting the cell or tissue. Contacting may occur in vivo by any method known in the art for administration of a solution or other composition containing the fluorenylated peptide or protein to an organism containing the cell or tissue.

Fluorenylation is typically carried out in an aqueous buffer or organic solvent suitable for the cargo molecule and in which fluorenylation can occur. More specifically, when the cargo molecule is a protein or peptide, fluorenylation is carried out in an aqueous buffer of appropriate pH which can be readily selected by one of ordinary skill in the art. Typically, fluorenylation of peptides and proteins is carried out at pH ranging from 5 to 8. Fluorenylation of peptides and proteins can be carried out at pH of 5.5 to 7.5.

Contacting with a cell or tissue is typically carried out in an aqueous buffer suitable for the cell or tissue. Contacting is typically carried out in an aqueous buffer of appropriate pH which can be readily selected by one of ordinary skill in the art. Typically, contacting is carried out at pH ranging from 5 to 8.

Contacting can include administration of an organism. Any suitable form of administration can be employed in the methods herein. The fluorenylated cargo molecules of this invention can, for example, be administered orally, topically, intravenously, intraperitoneally, subcutaneously, or intramuscularly, in any suitable dosage forms well known to those of ordinary skill in the pharmaceutical arts. The fluorenylated cargo molecules are optionally administered with a pharmaceutical carrier selected upon the basis of the chosen route of administration and standard pharmaceutical practice, such as, for example, as described in Remington's Pharmaceutical Sciences, 17th edition, ed. Alfonoso R. Gennaro, Mack Publishing Company, Easton, Pa. (1985), which is incorporated herein by reference in its entirety for suitable administration and carriers.

Cargo molecules include nucleic acids, peptides, proteins, small molecule drugs, reporters and labels (fluorescent labels or isotopic labels for example), imaging agents, contrast agents, particles carrying reactive functional groups, quantum dots carrying reactive functional groups, among others. In general any cargo molecule that it is desired to introduce into a cell can be employed in the methods of this invention. Cargo molecules include those having a biological activity. In specific embodiments, biological activity of interest of the cargo molecule is retained on fluorenylation or is recovered on selective removal of fluorenylation after delivery to a cell. In a specific embodiment, the fluorenylated cargo molecule retains at least 10% of a selected biological activity of the cargo molecule prior to fluorenylation. In other specific embodiments, the fluorenylated cargo molecule retains at least 50% of a selected biological activity of the cargo molecule prior to fluorenylation. In a further specific embodiment, the fluorenylated cargo molecule retains at least 80% of the activity of the cargo molecule prior to fluorenylation.

In a specific embodiment, the cargo protein is an enzyme. In a specific embodiment, the cargo protein is not glycosylated (i.e., is not a glycoprotein). In a specific embodiment, the fluorenylated cargo peptide or protein retains at least 10% of a selected biological activity of the protein prior to fluorenylation. In other specific embodiments, fluorenylated cargo peptide or protein retains at least 50% of a selected biological activity of the protein prior to fluorenylation. In a further specific embodiment, the fluorenylated cargo peptide or protein retains at least 80% of the activity of the peptide or protein prior to fluorenylation. Peptides and proteins include those having enzyme activity.

Cargo peptides include peptide ligands, cytotoxic peptides, bioactive peptides, diagnostic agents, among others. Cargo peptides include those having 2-1000 amino acids, 2-500 amino acids, 2-250 amino acids, 2-100 amino acids, 2-50 amino acids, and 2-25 amino acids and 2-10 amino acids.

Peptides and proteins include antibodies and functional fragments thereof, where the term antibody is used broadly herein. More specifically, antibodies include among others, monoclonal antibodies including humanized antibodies, human antibodies, interspecies antibodies, chimeric antibodies, human monoclonals, humanized monoclonals, interspecies antibodies made by any art-known methods. Functional fragments of antibodies include F(ab')2, F(ab)2, Fab', Fab, Fv, among others, as well as hybrid fragments. Additionally, antibodies include subfragments retaining the hypervariable, antigen-binding region of an immunoglobulin and preferably having a size similar to or smaller than a Fab' fragment. Such fragments and subfragments, including single chain fragments or multiple chain fragments, which incorporate an antigen-binding site and exhibit antibody function, are known in the art and can be prepared by methods that are well-known in the art, including by methods of preparing recombinant proteins. Antibodies and fragments thereof include therapeutic antibodies which are known in the art [Chames et al. 2009, 5]. This reference is incorporated by reference herein in its entirety for descriptions of therapeutic antibodies which can be employed in the present invention.

In a specific embodiment, the cargo molecule is a nucleic acid which may be RNA or DNA, or an analog of a nucleic acid which may be a peptide nucleic acid, a locked nucleic acid, or a phosphoramidate-morpholino oligomer. Other art-known nucleic acid analogs include carbamate-linked DNA, phosphorothioate-linked DNA, 2'-O-methyl RNA, phosphotriester-linked DNA or methylphosphonate-linked DNA. The cargo nucleic acid can be single- or double-stranded. The nucleic acid can be an oligonucleotide or analog thereof having 2-100, 2-50 or 2-25 bases. The nucleic acid can be SiRna, microRNa, antisense oligonucleotides, decoy DNA, plasmids or other nucleic acid structures such as minicircles. Nucleic acids and analogs thereof are available from commercial sources, can be isolated from natural source or can be prepared by methods that are well-known in the art.

In a specific embodiment, the fluorenylated cargo nucleic acid retains at least 10% of a selected biological activity of the nucleic acid prior to fluorenylation. In other specific embodiments, the fluorenylated cargo nucleic acid retains at least 50% of a selected biological activity of the nucleic acid prior to fluorenylation. In a further specific embodiment, the fluorenylated cargo nucleic acid retains at least 80% of the activity of the nucleic acid prior to fluorenylation. In a specific embodiment, the biological activity of the nucleic acid that is retained is binding to a complementary nucleic acid or binding to another biological molecule (e.g., a peptide or protein).

Cargo nucleic acids include those having 2-1000 bases, 2-500 bases, 2-250 bases, 2-100 bases, 2-50 bases, and 2-25 bases and 2-10 bases. Nucleic acids include nucleosides and analogs thereof.

In specific embodiments, cargo molecules of this invention include antibodies and various forms and fragments thereof. In specific embodiments, cargo molecules include transcription factors (proteins) which affect transcription of DNA to messenger RNA and thus affect expression of one or more genes. In specific embodiments, transcription factors include one or more DNA-binding domains. Transcription factors include, among others, tumor suppressors. A specific transcription factor of potential clinical interest is FOXO3 which functions as a trigger for apoptosis (see: Maiese et al. 2009, 6). One or more fluorenylation reagents of this invention, e.g., compounds of formula I, can be employed to fluorenylate transcription factors, including FOXO transcription factors, and more specifically FOXO3 to facilitate cell uptake thereof. Employing the reversible fluorenylation reagents herein, fluorenyl groups are removed after cell uptake.

In specific embodiments, cargo molecules include proteins that function as tumor suppressors. For example, cargo molecules include PTEN which is a phosphatidylinositol-3, 4,5-trisphosphate 3-phosphatase (Hopkins, et al. 2013, 7) PTEN contains a tensin-like domain as well as a phosphatase catalytic domain. PTEN negatively regulates the Akt/PKB signaling pathway functioning as a tumor suppressor. One or more fluorenylation reagents of this invention can be employed to fluorenylate PTEN to facilite cell uptake thereof. Employing the reversible fluorenylation reagents herein, fluorenyl group are removed after cell uptake.

In a specific embodiment, the cargo molecule is SCRIB, a scaffold protein which is involved in cell migration, cell polarity and cell proliferation [11]. One or more fluorenylation reagents of this invention can be employed to fluorenylate SCRIB to facilite cell uptake thereof. Employing the reversible fluorenylation reagents herein, fluorenyl groups are removed after cell uptake to facilitate entry into the cytosol of the cell.

In specific embodiments exemplified herein, fluorenylation reagents of this invention have been employed to derivatize GFP (Green fluorescent protein) with 2 or more fluorenyl groups to facilitate cellular uptake of the fluorescent protein. The reagents herein can be employed with various fluorescent proteins that are known in the art to facilitate their uptake into cells.

The present invention provides a method of reversibly labeling cargo molecules having one or more or two or more carboxylate groups for cellular uptake with optionally substituted fluorenyl groups, wherein the fluorenyl groups are removable by ester cleavage after cellular uptake. Cellular uptake is demonstrated herein to include at least in part uptake into the cytosol. In specific embodiments, the method employs diazofluorene reagents of formula I to react with carboxylate groups on the cargo molecule to form esters. Preferably 2 or more carboxylate groups of the cargo molecule are reacted to covalently attach fluorenyl groups, for example via ester linkages. After fluorenylation, the cargo molecule is placed in contact with a cell or tissue and the fluorenylated cargo molecule is taken up into the cell and at least in part into the cytosol. After uptake into the cell, the fluorenyl groups are removed within the cell, for example, by the action of cellular enzymes (e.g., esterases).

An aliphatic group as used herein refers to a monovalent non-aromatic hydrocarbon group which include straight chain, branched, or cyclic hydrocarbon groups which can be saturated or unsaturated with one or more double bonds or one or more triple bonds. Aliphatic groups may contain portions which are straight-chain or branched in combination with one or more carbon rings. Carbon rings of aliphatic groups may contain one or more double bonds or one or more triple bonds. Carbon rings of aliphatic groups can contain 3- to 10-membered rings. Such carbon rings may be fused and may be bicyclic or tricyclic. Aliphatic groups are optionally substituted with one or more non-hydrogen substituents where optional substituents are described herein. Unless otherwise specified, an aliphatic group can contain 1-20 carbon atoms or can contain 1-10 carbon atoms. Aliphatic groups include those containing 1-3, 1-6, and 1-8 carbon atoms. Aliphatic groups include, among others, alicyclic groups, alkyl groups, alkenyl groups and alkynyl groups.

Heteroaliphatic groups refer generally to aliphatic groups having 1 or more heteroatoms (other than C and H). Specifically heteroatoms of heteroaliphatic groups are selected from N, P, B, O or S. In more specific embodiments, heteroaliphatic groups contain one or more oxygens, one or more nitrogens and/or one or more sulfur atoms.

An alicylic group as used herein refers to a monovalent non-aromatic cyclic hydrocarbon group which can be saturated or unsaturated with one or more double bonds or one or more triple bonds. Alicyclic rings include those containing 3- to 10-membered carbon rings. Alicyclic groups include those containing one, two, three or more rings which may be fused or linked by straight chain or branched alkylene, alkenylene or alkynylene moieties. Alicyclic groups include bicyclic and tricyclic rings. Alicyclic groups include those in which one or more carbon rings are substituted with a straight-chain or branched alkyl, alkenyl or alkynyl group. To satisfy valence requirements, a ring atom may be substituted with hydrogen or optionally with non-hydrogen substituents as described herein. One or more carbons in an alicyclic group can be —CO— groups, i.e. a carbon can be substituted with an oxo (=O) moiety. Alicyclic groups are optionally substituted with one or more non-hydrogen substituents where optional substituents are described herein. Unless otherwise specified, an alicyclic group can contain 3-20 carbon atoms or can contain 3-12 carbon atoms. Alicyclic groups include those containing 3-6 and 3-8 carbon atoms. Alicyclic groups include among others cycloalkyl, cycloalkenyl, cyclopropyl, cyclobutyl, cyclopentyl, cyclopentadienyl, cyclohexyl, cyclohexenyl and cyclohexadienyl groups, all of which are optionally substituted.

A heterocyclic group as used herein refers to a monovalent non-aromatic cyclic hydrocarbon group wherein one or more of the rings contain one or more heteroatoms (e.g., N, S, O, or P) which rings can be saturated or unsaturated with one or more double bonds or one or more triple bonds. In specific embodiments of this invention, heterocyclic rings which are substituents of the compounds of formulas I, II and IIA do not contain boron atoms. In specific embodiments, heterocyclic rings are those having one nitrogen, and/or one oxygen and/or one sulfur. In specific embodiments, heterocyclic rings are those having one nitrogen, and/or one oxygen. In specific embodiments, heterocyclic rings are those having one nitrogen, or those having one oxygen or those having one sulfur. In specific embodiments, heterocyclic rings are those having one 5- or 6-member heterocylic ring. In specific embodiments, heterocyclic rings are those having one 5- or 6-member heterocyclic ring in which one or two ring members are nitrogen, and/or oxygen and/or sulfur. In specific embodiments, heterocyclic rings are those having one 5- or 6-member heterocyclic ring in which one or ring members are nitrogen, or oxygen or sulfur. Heterocyclic rings include those containing 3- to 10-membered rings where 1, 2 or 3 of the ring members are heteroatoms. Heterocyclic groups include those containing one, two, three or more rings which may be fused or linked by straight chain or branched alkylene, alkenylene or alkynylene moieties. Heterocyclic groups include bicyclic and tricyclic groups. Heterocyclic groups include those in which a heterocyclic ring is substituted with a straight-chain or branched alkyl, alkenyl or alkynyl group. To satisfy valence requirements, a ring atom may be substituted with hydrogen or optionally with non-hydrogen substituents as described herein. One or more carbons in a heterocyclic group can be —CO— groups. One or more carbons in a heterocyclic ring can be —CO— groups. Heterocyclic groups are optionally substituted with one or more non-hydrogen substituents where optional substituents are described herein. Ring carbons and, where chemically feasible, ring heteroatoms are optionally substituted. Unless otherwise specified, a heterocyclic group can contain 3-20 carbon atoms, can contain 3-12 carbon atoms or can contain 3-6 carbon atoms. Heterocyclic groups include those containing one or two 4-, 5- or 6-member rings at least one of which has one, two or three N, O or S atoms and wherein a ring optionally has one or two double bonds. Heterocyclic groups include those containing a single 5- or 6-member ring having one, two or three N, O or S atoms and optionally having one or two double bonds. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic groups include those having 5- or 6-member rings and two different heteroatom, e.g., N and O, O and S or N and S. Heterocyclic groups include those having 5- or 6-member rings and a single heteroatom, e.g., N S or O. In specific embodiments, heterocyclic groups do not include any boron atoms. Specific heterocyclic groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups, all of which are optionally substituted. In embodiments herein alicyclic or heterocyclic rings can be formed between certain substitution sites on the molecules of formula I, II and IIA. Such rings include the atom(s) of or between the sites of substitution and are defined with respect to the optional presence of heteroatoms, the optional presence of —CO— moieties and the optional presence of double bonds as are alicylic and heterocyclic groups. Unless otherwise specified such rings can contain 5-10-member rings and more preferably contain 5- to 8-member rings and more preferably 5- or 6-member rings. Ring atoms are optionally substituted as described herein.

Aryl groups are monovalent groups containing at least one aromatic ring. Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups may contain one or more non-aromatic alicyclic rings in addition to an aromatic ring. Aryl groups are optionally substituted with one or more non-hydrogen substituents as described herein. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. In a specific embodiment, aryl groups are not substituted with a boron-containing substituent, e.g., —B(OH)$_2$ or a —CH$_2$—B—O— moiety. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Unless otherwise specified, an aryl group can contain 5-20 carbon atoms or can contain 6-14 carbon atoms. Aryl groups also include those containing 6-12 carbon atoms.

Heteroaryl groups are monovalent groups having one or more aromatic rings in which at least one ring contains a heteroatom (a non-carbon ring atom). Heteroaryl groups include those having one or two heteroaromatic rings carrying 1, 2 or 3 heteroatoms and optionally having one 6-member aromatic ring. Heteroaryl groups can contain 5-20, 5-12 or 5-10 ring atoms. Heteroaryl groups include those having at least one aromatic ring containing a heteroatom and one or two alicyclic, heterocyclic or aryl ring groups. Heteroaryl groups include those having one aromatic ring containing a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include pyridinyl, pyrazinyl, pyrimidinyl, quinolinyl, and purinyl groups.

In embodiments herein aryl or heteroaryl rings can be formed between certain substitution sites on the molecules of formulas I, II or IIA. Such rings include the atom(s) of or between the sites of substitution and are defined with respect to the optional presence of heteroatoms. Unless otherwise specified such rings can contain 5- or 6-member rings and ring atoms are optionally substituted as defined herein.

Alkyl groups are monovalent groups and include straight-chain, and branched alkyl groups. Unless otherwise indicated alkyl and cycloalkyl groups include those having from 1 to 20 carbon atoms. Alkyl and cycloalkyl groups include those having 1 to 3 carbon atoms, those having from 4-7 carbon atoms and those having 8 or more carbon atoms.

Cyclic alkyl groups are alkyl groups having one or more carbon rings. Cyclic alkyl groups include those which have 1, 2 or 3 rings. Cyclic alkyl groups also include those having 3-10 carbon atoms. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry straight-chain or branched alkyl group substituents. Cyclic alkyl groups can include bicyclic and tricyclic alkyl groups.

Alkyl groups and cycloalkyl groups are optionally substituted with one or more non-hydrogen substituents as described herein. Specific alkyl groups include methyl, ethyl, n-propyl, iso-propyl, n-butyl, s-butyl, t-butyl, n-pentyl, branched-pentyl, n-hexyl, and branched hexyl, each of which is optionally substituted. Cycloalkyl groups include among others cyclopropyl, cyclobutyl, cyclopentyl, cyclohexyl, decalinyl, or norbornyl, each of which is optionally substituted. Substituted alkyl or cycloalkyl groups include fully halogenated or semihalogenated alkyl groups, such as alkyl or cycloalkyl groups having one or more hydrogens replaced with one or more fluorine atoms, chlorine atoms, bromine atoms and/or iodine atoms. Substituted alkyl or cycloalkyl groups include fully fluorinated or semifluorinated alkyl or cycloalkyl groups. Substituted alkyl or cycloalkyl groups include alkyl or cycloalkyl groups substituted with one or more hydroxyl groups. Substituted alkyl or cycloalkyl groups include alkyl or cycloalkyl groups substituted with two or more hydroxyl groups, particularly where two hydroxyl groups are substituted on adjacent carbon atoms.

Arylalkyl groups are monovalent alkyl groups substituted with one or more aryl groups wherein the alkyl groups optionally carry additional substituents and the aryl groups are optionally substituted. Specific arylalkyl groups are phenyl-substituted alkyl groups, e.g., benzyl groups or phenethyl groups which are optionally substituted Heteroarylalkyl groups are monovalent alkyl groups substituted with one or more heteroaryl groups wherein the alkyl groups optionally carry additional substituents and the aryl groups are optionally substituted.

Alkylaryl groups are monovalent aryl groups substituted with one or more alkyl groups wherein the alkyl groups optionally carry additional substituents and the aryl groups are further optionally substituted. Specific alkylaryl groups are alkyl-substituted phenyl groups such as o-, m- or p-tolyl groups which are optionally substituted.

Alkylheteroaryl groups are monovalent alkyl groups substituted with one or more heteroaryl groups wherein the alkyl groups optionally carry additional substituents and the heteroaryl groups are optionally substituted.

Alkenyl groups include monovalent straight-chain, and branched groups which contain one or more carbon-carbon double bonds. Unless otherwise indicated alkenyl and cycloalkenyl groups include those having from 2 to 20 carbon atoms. Alkenyl and cycloalkenyl groups include those having 2 to 4 carbon atoms and those having from 5-8 carbon atoms.

Cyclic alkenyl groups are alkenyl groups having one or more rings wherein at least one ring contains a double bond. Cyclic alkenyl groups include those which have 1, 2 or 3 rings wherein at least one ring contains a double bond. Cyclic alkenyl groups also include those having 3-10 carbon atoms. Cyclic alkenyl groups include those having a 5-, 6-, 7-, 8-, 9- or 10-member carbon ring and particularly those having a 5- or 6-member ring. The carbon rings in cyclic alkenyl groups can also carry straight-chain or branched alkyl or alkenyl group substituents. Cyclic alkenyl groups can include bicyclic and tricyclic alkyl groups wherein at least one ring contains a double bond.

Alkenyl and cycloalkenyl groups are optionally substituted with one or more non-hydrogen substituents as described herein. Specific alkenyl groups include ethylene, propenyl, butenyl, pentenyl, pentadienyl, hexylenyl, hexadienyl, cyclohexenyl, cyclohexadienyl, including all isomers thereof and all of which are optionally substituted. Specific cycloalkenyl groups include cyclopropenyl, cyclobutenyl, cyclopentenyl, cyclopentadienyl, cyclohexenyl, cyclohexadienyl, including all isomers thereof and all of which are optionally substituted. Substituted alkenyl or cycloalkenyl groups include fully halogenated or semihalogenated alkenyl or cycloalkenyl groups.

Alkynyl groups include mono-valent straight-chain, or branched alkynyl groups which contain one or more carbon-carbon triple bonds. Unless otherwise indicated alkynyl and cycloalkynyl groups include those having from 2 to 20 carbon atoms. Alkynyl and cycloalkynyl groups include those having 2 to 4 carbon atoms and those having from 5-8 carbon atoms. Cyclic alkynyl groups include those having one or more rings wherein at least one ring contains a triple bond. Cyclic alkynyl groups include those which have 1, 2 or 3 rings wherein at least one ring contains a triple bond. Cyclic alkynyl groups also include those having 3-10 carbon atoms. Cyclic alkynyl groups include those having a 5-, 6-, 7-, 8-, 9- or 10-member carbon ring and particularly those having a 5- or 6-member ring.

The carbon rings in cyclic alkynyl groups can also carry straight-chain or branched alkyl, alkenyl or alkynyl group substituents. Cyclic alkynyl groups can include bicyclic and tricyclic alkyl groups wherein at least one ring contains a triple bond. Alkynyl groups are optionally substituted with one or more non-hydrogen substituents as described herein.

An alkoxy group is an alkyl group as broadly discussed above, linked to oxygen, a monovalent —O-alkyl group. A cycloalkoxy group is a cycloalkyl groups as broadly discussed above, linked to oxygen, a monovalent —O-cycloalkyl group. An aryloxy group is an aryl group, as discussed above, linked to an oxygen, a monovalent —O-aryl. A heteroaryloxy group is a heteroaryl group as discussed above linked to an oxygen, a monovalent —O-heteroaryl. Alkenoxy, cycloalkenoxy, alkynoxy, cycloalkynoxy, alicycloxy, heterocycloxy groups are analogously defined. All of such groups are optionally substituted.

The number of carbon atoms in a given group, such as an alkyl group, can be indicated herein using the expression "Cm" where m is the number of carbon atoms. Thus, the expression "Cm1-Cm2" modifying a given chemical group indicates that the group can contain from m1 to m2 carbon atoms. For example, a C1-C6 alkyl group contains 1 to 6 carbon atoms, exclusive of carbons in any substituent on the alkyl group. Similar expressions can be used to indicate the number of atoms of N (nitrogen), O (oxygen) or other elements in a given group.

Optional substitution of groups herein includes substitution by one or more atoms or groups including alkyl, alkenyl, alkynyl, cycloalkyl, cycloalkenyl, cycloalkynyl, aryl, arylalkyl, halogen (e.g., Br—, I—, Cl—, F—), hydroxyl (—OH), nitro (—NO$_2$), cyano (—CN), isocyano (—NC), thiocyano (—SCN), isothiocyano (—NCS), sulfuryl (—SO$_2$), —N(R")$_2$, —COR", —COOR", —CON(R")$_2$, —NR"—CO—R", —NR"—CO—N(R")$_2$—, —CO—SR", —SO$_2$—NR"$_2$, —OR", or —SR", where each R", independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups. More specifically each —R" is independently selected from hydrogen, C1-C3 alkyl, C5 or C6 cycloalkyl, phenyl, or benzyl. More specifically, substituents include one or more alkyl, alkoxy, halogen, hydroxyl, nitro, cyano, isocyano (—NC), thiocyano (—SCN), isothiocyano (—NCS), or sulfuryl (—SO$_2$) groups.

In specific embodiments, groups which can be optionally substituted can carry 1, 2, 3, 4, 5 or 6 substituents. In specific embodiments, groups which can be optionally substituted can carry 1, 2, or 3 substituents. In specific embodiments, groups which can be optionally substituted can carry 1, or 2 substituents.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Fluorenylated compounds, fluorenylated oligopeptides, fluorenylated peptides, and fluorenylated proteins of the invention may be in the form of salts. Preferred salts are those that are biologically acceptable for ultimate applications of fluorenylated compounds, including fluorenylated peptides and proteins and which do not substantially detrimentally affect the effectiveness and properties of the free bases or free acids, and which are not biologically or otherwise undesirable. Salts may be prepared from addition of an organic or inorganic base to the free acid or addition of an organic or inorganic acid to the free base.

Exemplary salts of free bases are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, lactic acid, benzoic acid, cinnamic acid, mandelic acid, methanesulfonic acid, ethanesulfonic acid, p-toluenesulfonic acid, salicylic acid, trifluoroacetic acid, N-acetylcysteine and the like.

Exemplary salts of free acids formed with inorganic base include, but are not limited to, alkali metal salts (e.g., Li+, Na+, K+), alkaline earth metal salts (e.g., Ca2+, Mg2+), non-toxic heavy metal salts and ammonium (NH4+) and substituted ammonium (N(R')4+ salts, where R' is hydrogen, alkyl, or substituted alkyl, i.e., including, methyl, ethyl, or hydroxyethyl, specifically, trimethyl ammonium, triethyl ammonium, and triethanol ammonium salts), salts of cationic forms of lysine, arginine, N-ethylpiperidine, piperidine, and the like. Compounds of the invention can also be present in the form of zwitterions.

The term kit refers to kits for enhancement of cellular delivery and to kits for fluorenylating cargo molecules, particularly cargo molecules which are nucleic acids, peptides or proteins. In one embodiment, kits of this invention include one or more of the diazofluorene compounds of formula I or mixtures thereof and optionally reagents for ligating, conjugating or reacting the diazofluorene with a cargo molecule, e.g., a nucleic acid, peptide or protein to effect fluorenylation of the cargo molecule. In another embodiment, kits of this invention include one or more fluorenylated oligopeptides or fluorenylated amino acids of this invention and optionally reagents, such as one or more homo- or heterobifunctional crosslinking reagents, for ligating or conjugating the fluorenylated oligopeptide to a cargo molecule to effect fluorenylation of the cargo molecule. In yet another embodiment, kits of this invention may contain one or more fluorenylated amino acids and optionally one or more non-fluorenylated amino acids suitable for carrying out solid phase peptide synthesis of afluorenylated peptide including fluorenylated oligopeptide. In this embodiment, kits may also contain resin for carrying out solid phase peptide synthesis as well as reagents, solvents and other components needed for or useful for carrying out solid phase peptide synthesis.

Additionally such kits for synthesis of fluorenylated oligopeptides optionally contain one or more reagents, such one or more coupling reagents, or one or more homo- or heterobifunctional crosslinking reagents, for conjugation of the diazofluorene or fluorenylated oligopeptide to a peptide or protein to effect fluorenylation of the peptide or protein. Kits of the invention may also contain reagents for labeling of cargo molecules including reagents for labeling nucleic acids, peptides and proteins in addition to fluorenylation of cargo molecules. Kits for enhancing cellular uptake of a cargo molecule may further contain one or more cargo molecules which are to be fluorenylated for delivery to cells. Cargo molecules may further contain structural portions including cell penetrating peptides or targeting peptides, such as nuclear localization signals (such as are known in the art). Such kits may additionally comprise cells and cell growth media.

Kits of the invention may comprise a carrier being compartmentalized to receive in close confinement one or more containers, such as vials, test tubes, ampules, bottles and the like. Each of such container means comprises components or a mixture of components needed to perform the indicated fluorenylation, solid phase synthesis of fluorenylated oligopeptide, or enhancement of cellular uptake. The kits of the invention may further comprise one or more additional components (e.g., reagents and/or compounds) necessary or desirable for carrying out one or more particular applications of the compositions of the present invention. In general kits may also contain one or more buffers, control samples, carriers or recipients, vessels for carrying out one or more reactions, vessels for containing cells and the like, one or more additional compositions of the invention, one or more sets of instructions, and the like.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individually or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

General Methods:

Reagent chemicals were obtained from commercial sources and used without further purification unless otherwise noted. All glassware was flame-dried under vacuum, and reactions were performed under $N_2(g)$ unless indicated otherwise. If employed, dichloromethane, diethyl ether, tetrahydrofuran, and toluene were dried over a column of alumina and dimethylformamide and triethylamine were dried over alumina and purified further by passage through an isocyanate scrubbing column. Flash chromatography was performed with columns of 40-63 Å silica gel, 230-400 mesh (Silicycle, Québec City, Canada). Thin-layer chromatography (TLC) was performed on plates of EMD 250-μm silica 60-F254. The phrase "concentrated under reduced pressure" refers to the removal of solvents and other volatile materials using a rotary evaporator at water aspirator pressure (<20 torr) while maintaining the water-bath temperature below 40° C. Residual solvent was removed from samples at high vacuum (<0.1 torr). The term "high vacuum" refers to vacuum achieved by mechanical belt-drive oil pump. All NMR spectra were acquired at ambient temperature with a Bruker DMX-400 Avance, Bruker Avance III 500i with cryoprobe, or Bruker Avance III 500ii with cryoprobe spectrometer at the National Magnetic Resonance Facility at Madison (NMRFAM), and were referenced to TMS or a residual protic solvent. Electrospray ionization (ESI) mass spectrometry was performed with a Micromass LCT at the Mass Spectrometry Facility in the Department of Chemistry at the University of Wisconsin-Madison.

Example 1

Synthesis of 9-Azido-9H-fluorene 5 (See U.S. Pat. No. 8,350,014)

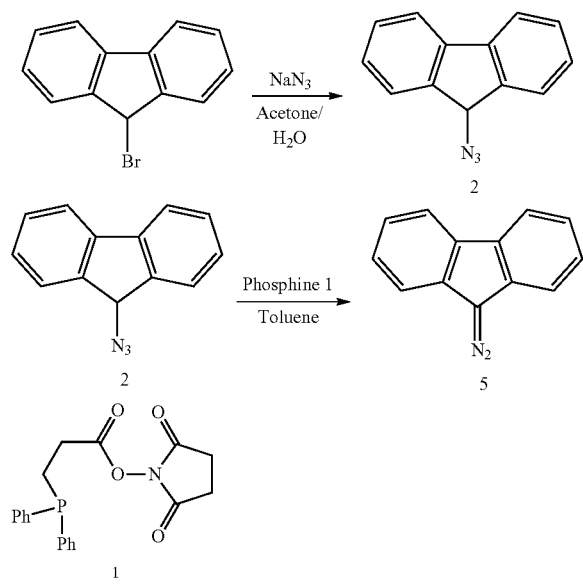

9-Bromo-9H-fluorene (1.00 g, 4.08 mmol) was dissolved in acetone (7 mL). To this was added a solution of $NaN_3$ (1.33 g, 20.4 mmol) in $H_2O$ (3 mL). The resulting solution was stirred overnight. Acetone was removed by concentration under reduced pressure. The resulting aqueous mixture was extracted with $CH_2Cl_2$ (2×15 mL), and the organic layers were combined, dried over $Na_2SO_4$(s), filtered, and concentrated under reduced pressure. The resulting solid residue was purified by silica gel flash chromatography, eluting with hexanes, to give azide 2 as a white solid (0.74 g, 3.57 mmol, 87% yield).

Data for 2: $^1$H NMR (400 MHz, $CDCl_3$) δ=7.74 (d, 2H, J=7.4 Hz, Ar.), 7.66 (d, 2H, J=7.4 Hz, Ar.), 7.47 (t, 2H, J=7.4 Hz, Ar.), 7.39 (t, 2H, J=7.4 Hz, Ar.), 5.23 (s, 1H, $CHN_3$). $^{13}$C NMR (100 MHz, $CDCl_3$) δ=141.6, 140.7, 129.4, 127.9, 125.2, 120.3, 64.3.

Treatment of 9-azido-fluorene 2 with phosphine 1 under anhydrous conditions at low temperature (toluene, 0° C.), followed by loading the red solution directly on basic alumina (Grade 5) and eluting with 10% $CH_2Cl_2$/hexanes provided 9-diazo-fluorene 5 which was isolated in 85% yield and excellent purity (96%). Apparently, thermal fragmentation of the putative triazenophosphonium salt, which more than likely exists in its neutral $λ^5$-phosphorane form is suppressed sufficiently for this substrate under the reaction conditions. The low temperature and low polarity of the solvent probably contribute to that greater stability. Under the standard conditions ($THF/H_2O$), incomplete conversion of the azide 2 and contamination of the diazo-compound 5 with substantial amounts of other products, probably arising from alternative triazene decomposition and dimerization of the diazo-compound, were apparent.

Specifically, a solution of 9-azido-9H-fluorene 2 (62 mg, 0.303 mmol) in anhydrous toluene (1.5 mL) was placed under Ar(g) and cooled to 0° C. A solution of phosphine 1 in dry toluene (1 mL) was then added dropwise over 10 min whilst maintaining the temperature at 0° C. The solution was then stirred for 5 h at 0° C. The solution was then allowed to warm to room temperature and stirred overnight. The resulting red solution (with white precipitate) was placed directly on a column of alumina (Basic, Grade 5) and eluted with hexanes to give diazo-compound 5 as a red solid (51 mg), which NMR analysis showed to be approximately 96% pure (the remainder being azide 2), thus giving an 85% yield.

Data for 5: $^1$H NMR (400 MHz, $CDCl_3$) δ=7.98 (d, 2H, J=7.5 Hz, Ar.), 7.54 (d, 2H, J=7.5 Hz, Ar.), 7.42 (t, 2H, J=7.5 Hz, Ar.), 7.36 (t, 2H, J=7.5 Hz, Ar.). $^{13}$C NMR (100 MHz, $CDCl_3$) δ=133.0, 131.4, 126.3, 124.5, 121.0, 119.3. 63.4. {Lit. $^1$H NMR (400 MHz, $CDCl_3$) δ=7.97 (ddd, 2H, J=7.6, 1.2, 0.8 Hz, Ar.), 7.53 (ddd, 2H, J=7.7, 1.2, 0.8 Hz, Ar.), 7.42 (td, 2H, J=7.4, 1.2 Hz, Ar.), 7.36 (td, 2H, J=7.5, 1.2, Ar.). $^{13}$C NMR (100 MHz, $CDCl_3$) δ=132.94, 131.41, 126.28, 124.48, 120.92, 119.27, 63.37.

Example 2

RNAse A Labeling (See U.S. Pending application Ser. No. 14/212,381, Filed Mar. 14, 2014, Appendix A)

Ribonuclease A (0.001 g, 0.073 μmol) was dissolved in MES buffer (10 mM, pH=5.5, 0.1 mL) and a stock solution of diazofluorene 5 in acetonitrile was made (Stock solution: 0.001 g, 7.30 μmol, 1 mL $CH_3CN$). The stock solution of diazo compound (0.1 mL, 0.730 μmol) was added to the ribonuclease solution and the reaction was allowed to stir 4 h at 37° C. Any remaining diazo compound was then quenched by adding 0.1 M acetic acid (0.1 mL) and the reaction was concentrated and the extent of labeling was determined by MALDI spectroscopy to be ~3 labels per RNase A.

Each respective labeled sample of RNase A (0.001 g, 0.073 micromol) was dissolved in MES buffer (10 mM, pH=5.5, 0.2 mL) and treated with *Saccharomyces cerevisiae* esterase (0.001 g) for 24 h at 37° C. The reactions were then analyzed by MALDI-MS to confirm the regeneration of unlabeled RNase A.

Example 3

Green Fluorescent Protein (GFP) Labeling

Figure 1B:
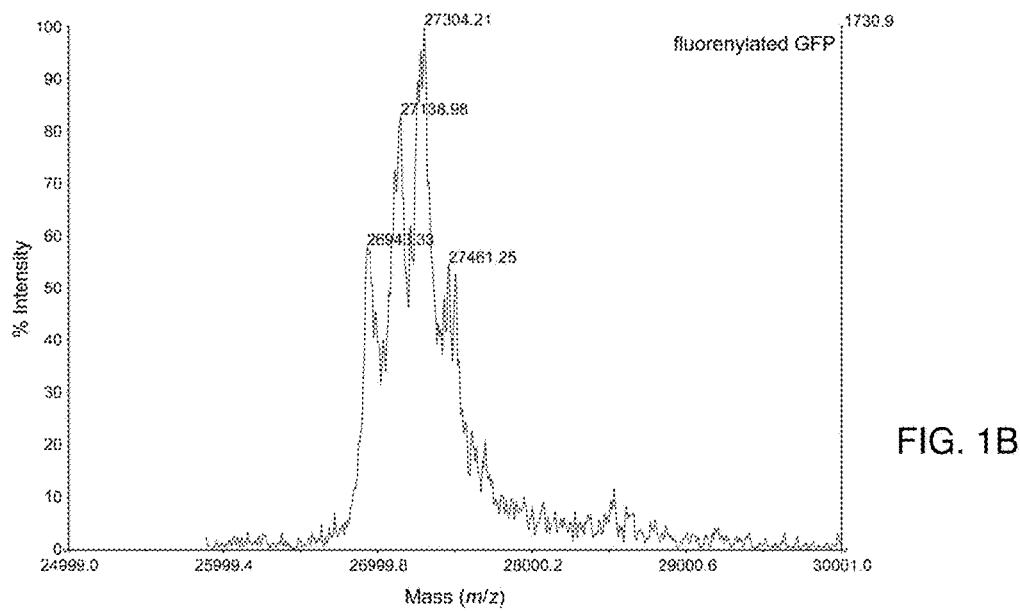

As a model protein, a variant of the Green Fluorescent Protein (GFP) was used. This variant was based on the "superfolder" variant [9]. Specifically, the variant has the "superfolder" substitutions: F64L, S65T, F99S, M153T, V163A, S30R, Y154F, I171V, A206V, N391, T105K, E111V, I128T, K166T, I167V, S205T, L221H, F223Y, and T225N. The variant also has a $His_6$ tag at its N terminus and a TEV-protease cleavage cite between the $His_6$ tag and the remainder of the amino-acid sequence. This GFP variant is labelled with diazofluorene, using the following procedure. Diazofluorene 5 (1.25 µmol) in acetonitrile (500 µL) was added to GFP (250 µM, 0.125 µmol) in 10 mM MES-NaOH buffer, pH 5.5 (500 µL). The final solution was 1:1 acetonitrile/buffer with a 10× molar excess of diazofluorene over protein. This solution was incubated at room temperature for 24 h on a nutator. The protein was subsequently dialyzed against PBS, pH 7.3 and filtered through a 0.45 µm filter. Labeling reaction resulted in GFP labeled with 1-3 fluorenyl groups as shown by MALDI-TOF mass spectrometery (FIGS. 1 A and 1B).

Example 4

Figure 2A:
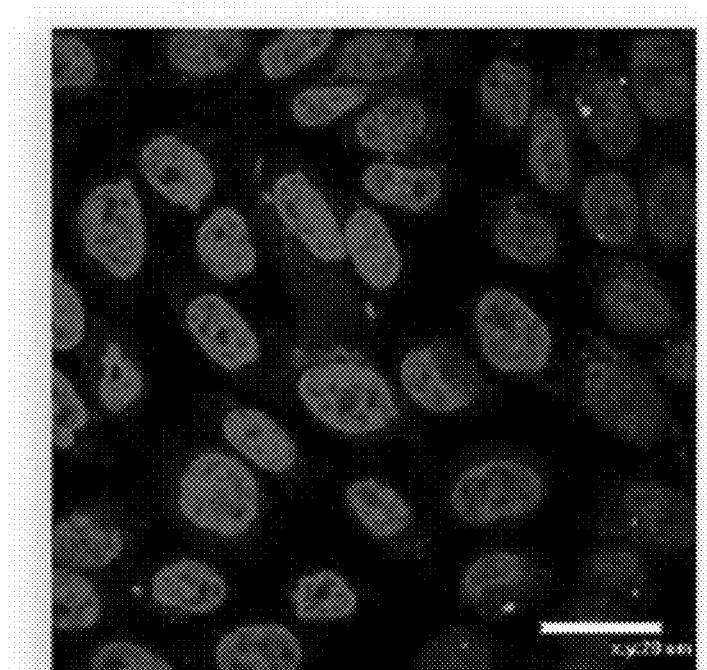
FIGS. 2A-2C illustrate uptake of GFP (control), cell-penetrating GFP and fluorenylated GFP into cells.
Figure 2B:
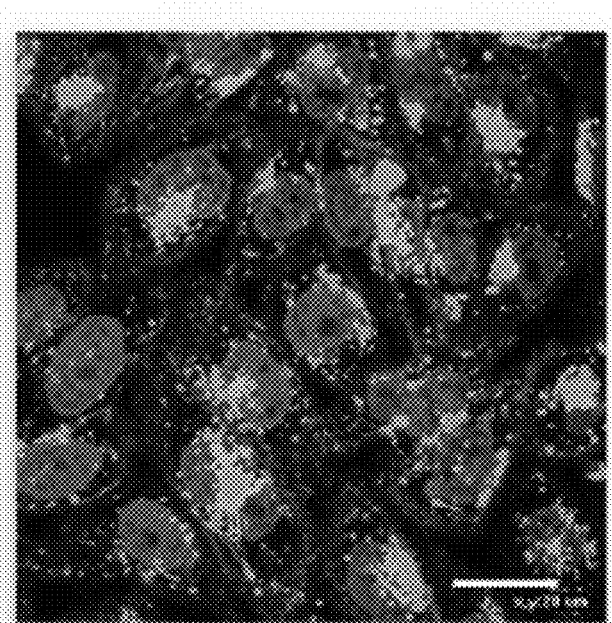
Figure 2C:
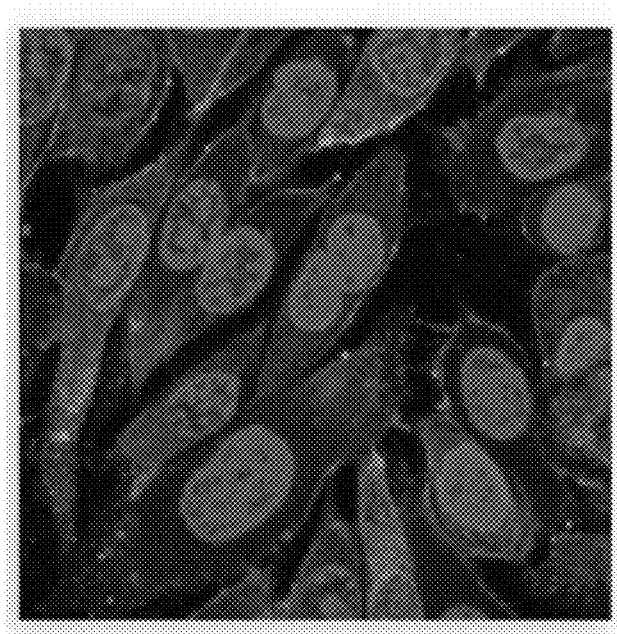

CHO K1 cells were obtained from American Type Culture Collection (ATCC) and maintained according to the recommended procedures. Cells were grown at 37° C. under 5% $CO_2$ in F12K medium supplemented with fetal bovine serum (10% v/v), penicillin (100 units/mL), and streptomycin (100 µg/mL). On the day of an experiment, cells were plated at a density of 50,000 cells/well in a glass 8-µwell slide (Ibidi) and allowed to adhere for 12 h in the F12K medium. The green fluorescent protein (GFP) variant was then added: GFP (10 microM), cell-penetrating GFP (to 5 microM), or fluorenylated GFP (10 microM). Fluorenylated GFP is labelled as in Example 2. Cell-penetrating GFP contains five Asp/Glu to Arg substitutions and multiple "superfold mutations" (see above) and as described in U.S. Pat. No. 7,452,973 and Fuchs et al. The incubation was continued for 4 h at 37° C. Cells were then washed with Dulbecco's phosphate-buffered saline containing fetal bovine serum (1% v/v), and stained with Hoechst 33342 dye. Cells were imaged while live in medium with a Nikon Eclipse C1 scanning confocal microscope. FIGS. 2 A-2C illustrate the results of this experiment for GFP (control), cell-penetrating GFP and fluorenylated GFP, respectively. Punctate or diffuse staining indicates localization in endosomes or the cytosol, respectively. Fluorenylated GFP is clearly taken up into the cytosol.

The mechanism of cytosolic uptake is unclear. Without wishing to be bound by any particular mechanism of uptake, it is currently believed that cytosolic uptake involves receptor mediated uptake facilitated by the fluorene moiety.

REFERENCES

[1] a) S. D. Patil, D. G. Rhodes, D. J. Burgess, *AAPS J.* 2005, 7, E61-77; b) D. K. Malik, S. Baboota, A. Ahuja, S. Hasan, J. Ali, *Curr. Drug Deliv.* 2007, 4, 141-151; c) M. S. Shim, Y. J. Kwon, FEBS J. 2010, 277, 4814-4827.

[2] a) Y. Gao, G. Gao, Y. He, T. Liu, R. Qi, *Mini Rev. Med. Chem.* 2008, 8, 889-900; b) M. Rapoport, H. Lorberboum-Galski, *Expert Opin. Drug Deliv.* 2009, 6, 453-463; c) X. Sun, N. Zhang, *Mini Rev. Med. Chem.* 2010, 10, 108-125; d) N. Schmidt, A. Mishra, G. H. Lai, G. C. Wong, *FEBS Lett.* 2010, 584, 1806-1813.

[3] a) X. Zhao, H. Li, R. J. Lee, *Expert Opin. Drug Deliv.* 2008, 5, 309-319; b) S. S. Rizk, A. Luchniak, S. Uysal, C. M. Brawley, R. S. Rock, A. A. Kossiakoff, *Proc. Natl. Acad. Sci. USA* 2009, 106, 11011-11015; c) C. Mohanty, M. Das, J. R. Kanwar, S. K. Sahoo, *Curr. Drug Deliv.* 2011, 8, 45-58.

[4] Marschall, A. L. J. et al. (January/February 2011) "Targeting Antibodies to the Cytoplasm," MAbs v. 3(1): 3-16 Landes Bioscience.

[5] Chames, P. Van Regenmortel, M. Weiss, E. & Baty, D. Therapeutic antibodies: successes, limitations and hopes for the future. Br J Pharmacol. 2009 May; 157(2): 220-233.

[6] Maiese, K.; Chong, Z. Z.; Shang, Y. C.; Hou, J. L. "FOXO" in sight: Targeting Foxo proteins from conception to cancer" *Med. Res. Rev.* 2009, 29, 395-418.

[7] P Hopkins et al. Science 2013, 341, 399-40.

[8] F. G. Bordwell (1988) Acc. Chem. Res. 21, 456, 463. A Table of pKa data of acidity of various organic compounds in DMSO is found at http://www.chem.wisc.edu/areas/reich/pkatable/; F. G. Bordwell et al. J. Am. Chem. Soc. 1975, 97, 7006; F. G. Bordwell et al. J. Org. Chem. 1980, 45, 3325; F. G. Bordwell et al. J. Org. Chem. 1981, 46, 632; F. G. Bordwell et al. J. Am. Chem. Soc. 1983, 105, 6188; F. G. Bordwell et al. J. Org. Chem. 1990, 55, 3330; F. G. Bordwell et al. J. Org. Chem. 1991, 56, 4218; F. G. Bordwell et al. Can. J. Chem. 1990, 68, 1714.

[9] Pédelacq, J. D.; Cabantous, S.; Tran, T.; Terwilliger, T. C.; Waldo, G. S. *Nat. Biotechnol.* 2006, 24, 79-88.

[10] Fuchs, S. M. and Raines, R. T. "Arginine Grafting to Endow Cell Permeability" ACS Cell Biology Vol. 2(3): 167-170.

[11] Martin-Belmonte, F.; Perez-Moreno, M. *Nat. Rev. Cancer* 2012, 12, 23-38.

The invention claimed is:

1. A method for increasing cellular uptake of a protein by fluorenylating the protein by covalently bonding one or more optionally substituted fluorenyl groups to the protein and contacting a cell with the fluorenylated protein, wherein cellular uptake of the fluorenylated protein is increased compared to the protein without fluorenylation, wherein fluorenylation is carried out by esterification of one or more carboxylate groups of the protein.

2. The method of claim 1 wherein fluorenylation is carried out by esterification of one or more carboxylate groups of the protein with a diazofluorene of formula I:

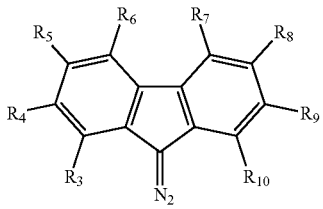

or salts thereof, wherein:
- $R_3$-$R_{10}$ are selected from hydrogen, alkyl, alkoxy, alkenyl, alkenoxy, alkynyl, alkynoxy, aryl, aryl oxy, alkylaryl, alkylaryloxy, arylalkyl, arylalkyloxy, heteroaryl, heteroaryloxy, carbocyclic, carbocyclyloxy, heterocyclic or heterocyclyloxy groups each of which is optionally substituted; or
- $R_3$-$R_{10}$ are selected from non-hydrogen substituents selected from halogens, hydroxyl, nitro groups, cyano, isocyano, thiocyano, isothiocyano, sulfuryl, —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted, or two of $R_3$-$R_{10}$ are linked together to form an optionally substituted carbocyclic, aryl, heterocyclic or heteroaryl ring wherein one or two carbons of the ring are optionally replaced with —CO— and the carbocyclic or heterocyclic rings are saturated or unsaturated.

3. The method of claim 2, wherein the compound of formula I is 9-diazofluorene.

4. The method of claim 1, wherein the protein is an antibody or functional fragment thereof or is an enzyme.

5. The method of claim 4, wherein fluorenylation is carried out by esterification of one or more carboxylate groups of the protein with 9-diazofluorene.

6. The method of claim 1, which is carried out in vitro.

7. The method of claim 1, wherein the protein retains at least 10% of its biological activity on fluorenylation compared to the protein without fluorenylation.

8. The method of claim 1, wherein two or more carboxylate groups of the protein are fluorenylated.

9. The method of claim 1, wherein the fluorenylated protein is taken up at least in part into the cytosol of the cell.

10. The method of claim 9, wherein after uptake into the cell, the fluorenyl groups of the fluorenylated protein are removed within the cell.

11. The method of claim 1, wherein fluorenylation is carried out by esterification of one or more carboxylate groups of the protein with a diazofluorene.

12. The method of claim 1, wherein increasing cellular uptake represents an enhancement of 2-fold or higher of cellular uptake of the fluorenylated protein compared to cellular uptake of the corresponding protein that is not fluorenylated.

13. The method of claim 9, wherein increasing cellular uptake represents an enhancement of 2-fold or higher of cellular uptake into the cytosol of the fluroenylated protein compared to cellular uptake into the cytosol of the protein that is not fluorenylated.

* * * * *